(12) United States Patent
Granier et al.

(10) Patent No.: US 8,093,204 B2
(45) Date of Patent: Jan. 10, 2012

(54) ORGANIC COMPOUNDS

(75) Inventors: Thierry Granier, Duebendorf (CH); Andreas Hanhart, Uster (CH); Jerzy A. Bajgrowicz, Zürich (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 12/602,357

(22) PCT Filed: Jun. 3, 2008

(86) PCT No.: PCT/CH2008/000248
§ 371 (c)(1),
(2), (4) Date: Mar. 16, 2010

(87) PCT Pub. No.: WO2008/148235
PCT Pub. Date: Nov. 12, 2008

(65) Prior Publication Data
US 2010/0173821 A1    Jul. 8, 2010

(30) Foreign Application Priority Data

Jun. 5, 2007 (GB) .................................. 0710703.0

(51) Int. Cl.
*A61K 8/18* (2006.01)
*A61K 8/00* (2006.01)
*A61Q 13/00* (2006.01)
*C07C 49/00* (2006.01)
*C07F 15/00* (2006.01)

(52) U.S. Cl. .............. 512/22; 512/1; 568/300; 568/303; 568/376; 568/377

(58) Field of Classification Search ................ 512/1, 22; 568/376, 377, 300, 303
See application file for complete search history.

(56) References Cited

U.S. PATENT DOCUMENTS 3,946,078 A    3/1976   Rautenstrauch et al.
4,760,050 A *  7/1988   Van Der Weerdt et al. ... 568/376

FOREIGN PATENT DOCUMENTS

DE    2242751 A1    3/1973
EP    0009540 A2    4/1980
WO    2002/14243 A1 2/2002

* cited by examiner

*Primary Examiner* — Milton I Cano
*Assistant Examiner* — Aaron Greso
(74) *Attorney, Agent, or Firm* — Norris McLaughlin & Marcus PA

(57) ABSTRACT

The present invention relates to compounds useful as fragrance ingredients of formula (I)

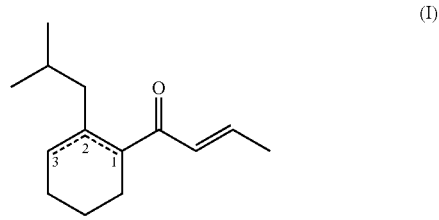

wherein
the bond between C-1 and C-2 is a single bond and the dotted line together with the bond between C-2 and C-3 represents a double bond; or
the bond between C-2 and C-3 is a single bond and the dotted line together with the bond between C-1 and C-2 represents a double bond.

3 Claims, No Drawings

ORGANIC COMPOUNDS

This application is a 35 U.S.C. §371 national phase application of International Application number PCT/CH2008/000248, filed 3 Jun. 2008, and claims priority to UK Patent Application No. GB0710703.0, filed 5 Jun. 2007.

The present invention refers to 1-(2-isobutylcyclohex-1/2-enyl)but-2-en-1-one, to a method of their production and to fragrance and flavour compositions comprising it.

In the fragrance industry there is a constant demand for new compounds that enhance or improve on odour notes. Surprisingly, we found that 1-(2-isobutylcyclohex-1-enyl)but-2-en-1-one and 1-(2-isobutylcyclohex-2-enyl)but-2-en-1-one, alone or as isomeric mixture display a powerful and substantive combination of fruity, floral, green, rosy odour notes backed by metallic, sweet, woody undertones that is on its all very reminiscent of the natural geranium scent.

The geranium scent is very often used in the creation of floral accords, more specifically in rosy notes but also in aldehydic notes. The use of geranium notes is, however, not restricted to feminine fragrances. Indeed geranium notes also find an application in the creation of masculine fragrances (fougère), and thus play a major role for the creation of fine fragrance.

The present invention refers in one of its aspects to a compound of formula (I)

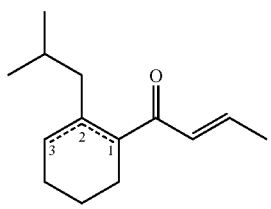

(I)

wherein
the bond between C-1 and C-2 is a single bond and the dotted line together with the bond between C-2 and C-3 represents a double bond; or
the bond between C-2 and C-3 is a single bond and the dotted line together with the bond between C-1 and C-2 represents a double bond.

The compounds of the present invention may comprise a chiral centre and as such may exist as a mixture of stereoisomers, or they may me resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis The compounds according to the present invention may be used alone or in combination with known odorant molecules selected from the extensive range of natural and synthetic molecules currently available, such as essential oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art, e.g., solvents such as dipropylen glycol, isopropylmyristate, and triethylcitrate The following list comprises examples of known odorant molecules, which may be combined with the compounds of the present invention:

essential oils and extracts, e.g. oak moss absolute, basil oil, tropical fruit oils, such as bergamot oil and mandarine oil, mastic absolute, myrtle oil, palmarosa oil, patchouli oil, petitgrain oil, wormwood oil, lavender oil, rose oil, jasmin oil, ylang-ylang oil and sandalwood oil.

alcohols, e.g. cis-3-hexenol, cinnamic alcohol, citronellol, Ebanol®, eugenol, farnesol, geraniol, menthol, nerol, rhodinol, Super Muguet™, linalool, phenylethyl alcohol, Sandalore®, terpineol and Timberol® (1-(2,2,6-Trimethylcyclohexyl)hexan-3-ol).

aldehydes and ketones, e.g. citral, hydroxycitronellal, Lilial®, methylnonylacetaldehyde, anisaldehyde, allylionone, verbenone, nootkatone, geranylacetone, α-amylcinnamic aldehyde, Georgywood™, hydroxycitronellal, Iso E Super®, Isoraldeine® (methylionone), Hedione®, maltol, methyl cedryl ketone, and vanillin.

ethers and acetals, e.g. Ambrox®, geranyl methyl ether, rose oxide or Spirambrene®.

esters and lactones, e.g. benzyl acetate, cedryl actetate, γ-decalactone, Helvetolide®, γ-undecalactone, vetivenyl acetate, cinnamyl propionate, citronellyl acetate, decyl acetate, dimethylbenzylcarbinyl acetate, ethyl acetoacetate, cis-3-hexenyl isobutyrate, linalyl acetate and geranyl acetate.

macrocycles, e.g. ambrettolide, ethylene brassylate or Exaltolide®.

heterocycles, e.g. isobutylquinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.0001 to 2 weight percent of the application. In one embodiment, compounds of the present invention may be employed in a fabric softener in an amount of from 0.0001 to 0.005 weight percent. In another embodiment, compounds of the present invention may be used in an alcoholic solution in amounts of from 0.01 to 3 weight percent, more preferably between 0.5 and 2 weight percent. However, these values are given only by way of example, since the experienced perfumer may also achieve effects or may create novel accords with lower or higher concentrations, e.g. up to about 20 weight percent based on the fragrance composition.

The compounds of the present invention may be employed into the fragrance application simply by directly mixing the fragrance composition with the fragrance application, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application and consumer products resulting therefrom. The method comprises the incorporation therein of a compound of formula (I) as a fragrance ingredient, either by directly admixing the compound to the application or by admixing a fragrance composition comprising a compound of formula (I), which may then be mixed to a fragrance application, using conventional techniques and methods. Through the addition of an olfactory acceptable amount of a compound of the present invention, the odour notes of a fragrance application will be improved, enhanced or modified.

Thus, the invention furthermore provides a method for improving, enhancing or modifying a fragrance application through the addition thereto of an olfactory acceptable amount of a compound of formula (I), or a mixture thereof.

The invention also provides a fragrance application comprising:
a) as odorant a compound of formula (I) or a mixture thereof; and
b) a consumer product base.

As used herein, "fragrance application" means any products, such as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant. This list of products is given by way of illustration and is not to be regarded as being in any way limiting.

The compounds of formula (I) may be prepared by acylation of 1-isobutyl-cyclohexene with crotonyl chloride or crotonic anhydride in the presence of a Lewis acid leading to the monoconjugated butanone, i.e. a compound of formula (I) wherein the bond between C-1 and C-2 is a single bond and the dotted line together with the bond between C-2 and C-3 represents a double bond, that could be isomerized to the diconjugated butanone, i.e. a compound of formula (I) wherein the bond between C-2 and C-3 is a single bond and the dotted line together with the bond between C-1 and C-2 represents a double bond, by heating in toluene in the presence of an acid e.g. PTSA.

The invention is now further described with reference to the following non-limiting examples. These examples are for the purpose of illustration only and it is understood that variations and modifications can be made by one skilled in the art.

EXAMPLE 1

(E)-1-(2-isobutylcyclohex-2-enyl)but-2-en-1-one a) 1-isobutylcyclohexanol

At −60° C., a solution of 1.7M tert-butyllithium in pentane (1000 ml, 1.7 mol, 2.1 eq.) in diethyl ether (800 ml) was treated dropwise within 1 h with isobutyl iodide (157 g, 0.81 mol, 1.0 eq.). The resulting solution was stirred at −70° C. for 45 min., warmed to 10° C., cooled to −70° C., and treated at this temperature within 4 h with cyclohexanone (100.7 ml, 0.971 mol, 1.2 eq.). At the end of the addition, the reaction mixture was allowed to reach room temperature before being poured into ice/$H_2O$ (500 ml) and acidified with concentrated HCl. The water phase was extracted with diethyl ether (300 ml) and the combined organic phases were washed with water (400 ml) and aqueous saturated NaCl solution (500 ml), dried (50 g $MgSO_4$) and the solvent evaporated to give the crude 1-isobutylcyclohexanol (148 g).

b) 1-isobutylcyclohex-1-ene

In a flask equiped with a Vigreux-distillation apparatus, crude 1-isobutylcyclohexanol (200 g, 1.28 mol) was treated with phosphoric acid (100 g) and heated at 145° C. under vacuum (170 mbar). While 1-isobutylcyclohex-1-ene and water distilled (boiling point 60° C.), a second fraction of 1-isobutylcyclohexanol (492 g, 3.15 mol) was added dropwise in the reaction flask. At the end of the addition, the thick reaction mixture was diluted with paraffin oil (100 ml) and additional phosphoric acid (50 g) and heated further (vacuum from 170 to 40 mbar). The distillate was decanted and the water phase extracted with pentane (100 ml). The combined org. phases were dried ($MgSO_4$) and the solvent evaporated to give 1-isobutylcyclohex-1-ene (448 g, 78%).

c) (E)-1-(2-isobutylcyclohex-2-enyl)but-2-en-1-one

At −70° C., a solution of tin tetrachloride (533 ml, 4.54 mol, 1.4 eq.) in dichloromethane (2.5 l) was treated with crotonyl chloride (350 ml, 90%, 3.24 mol, 1.0 eq.). The resulting solution was stirred for 30 min. and treated within 1.5 h with a solution of 1-isobutylcyclohex-1-ene (448 g, 3.24 mol) in dichloromethane (400 ml). The resulting mixture was stirred for 1 h at −70° C. and poured into ice/$H_2O$. The org. phase was first washed with concentrated NaOH then with $H_2O$, dried ($MgSO_4$), and the solvent evaporated. Short-path Vigreux-distillation (0.15 mbar, bath temperature: 160° C.) of the crude product (592 g) gave a fraction (495 g, boiling range: 90-130° C.) that was redistilled using again a short-path Vigreux-column (0.11 mbar, bath temperature: 160° C.) to give (E)-1-(2-isobutylcyclohex-2-enyl)but-2-en-1-one (202 g, 30%). Boiling point: 120° C. (0.11 mbar).

$^1$H-NMR (400 MHz, $CDCl_3$): δ6.94 (dq, J=6.8, 15.4, H—C(3)), 6.25 (dq, J=1.7, 15.4, H—C(2)), 5.68-5.65 (m, H—C(3')), 3.29-3.23 (m, 1H), 2.16-1.97 (m, 2H), 1.90 (dd, J=1.6, 6.9, MeC(3)), 1.90-1.81 (m, 2H), 1.76-1.59 (m, 4H), 1.56-1.43 (m, 1H), 0.85 (t, J=6.3, MeCH), 0.79 (t, J=6.1, MeCH).

$^{13}$C-NMR (100 MHz, $CDCl_3$): δ202.00 (s, CO), 142.59 (d, C(3)), 133.97 (s, C(2')), 129.68 (d), 126.13 (d), 49.70 (d, C(1')), 45.98 (t), 26.85 (t), 25.90 (d), 25.06 (t), 23.23, 21.54 (2q, $Me_2CH$), 19.87 (t), 18.18 (q, C(4)).

MS (EI): 206 (6), 191 (1), 163 (13), 150 (1), 149 (3), 137 (5), 136 (3), 121 (2), 108 (1), 107 (1), 95 (9), 94 (3), 93 (4), 91 (5), 81 (38), 79 (11), 69 (100), 41 (25).

IR: $v_{max}$ 2951, 2867, 2838, 1694, 1668, 1628, 1444, 1366, 1314, 1289, 1250, 1189, 1126, 1085, 1059, 971, 912, 880, 798 $cm^{-1}$.

Odour description: fruity, rosy, green, carrot.

EXAMPLE 2

(E)-1-(2-isobutylcyclohex-1-enyl)but-2-en-1-one/
(E)-1-(2-isobutylcyclohex-2-enyl)but-2-en-1-one
(60:40)

A solution of (E)-1-(2-isobutylcyclohex-2-en-1-one (202 g, 0.979 mol) in toluene (3 l) was treated with p-toluenesulfonic acid monohydrate (3.7 g, 19.5 mmol), refluxed during 18 h and poured into water. The org. phase was dried ($MgSO_4$) and concentrated. Short-path Vigreux-distillation (0.11 mbar, bath temperature: 140-160° C.) of the crude product (181 g, 68:32 mixture of (E)-1-(2-isobutylcyclohex-1-enyl)but-2-en-1-one/(E)-1-(2-isobutylcyclohex-2-enyl)but-2-en-1-one) gave a mixture of butenones (181 g, 90%, boiling range 90-110° C.) that was redistilled (0.08 mbar, bath temperature: 150° C.) using a Sulzer-column affording a 60:40 mixture of (E)-1-(2-isobutylcyclohex-1-enyl)but-2-en-1-one/(E)-1-(2-isobutylcyclohex-2-enyl)but-2-en-1-one (145.6 g, 72%).

Boiling point: 98° C. (0.08 mbar).

Odour description: geranium-like (fruity, green, metallic, herbaceous, sweet, woody).

Data of (E)-1-(2-isobutylcyclohex-1-enyl)but-2-en-1-one:

$^1$H-NMR (400 MHz, CDCl$_3$): δ6.80 (dq, J=6.8, 15.8, H—C(3)), 6.25 (dq, J=1.7, 15.7, H—C(2)), 2.18-2.12 (m, 2H), 2.04-1.99 (m, 2H), 1.92 (dd, J=1.8, 6.8, MeC(3)), 1.90-1.87 (m, 2H), 1.83-1.73 (m, 1H), 1.67-1.60 (m, 4H), 0.81 (t, J=6.6, Me$_2$CH).

$^{13}$C-NMR (100 MHz, CDCl$_3$): δ201.07 (s, CO), 145.10 (d, C(3)), 136.96 (s, C(2')), 133.96 (s, C(1')), 132.33 (d, C(2)), 43.69 (t), 28.65 (t), 27.45 (t), 26.41 (d), 22.57 (t), 22.39 (q, Me$_2$CH), 22.34 (t), 18.31 (q, C(4)).

MS (EI): 206 (2), 191 (15), 163 (100), 150 (5), 149 (15), 135 (9), 121 (79), 107 (17), 105 (7), 93 (11), 91 (17), 81 (10), 79 (18), 77 (15), 69 (33), 67 (10), 55 (15), 53 (8), 43 (13), 41 (38).

EXAMPLE 3

(E)-1-(2-isobutylcyclohex-1-enyl)but-2-en-1-one/ (E)-1-(2-isobutylcyclohex-2-enyl)but-2-en-1-one (91:9)

A solution of (E)-1-(2-isobutylcyclohex-2-enyl)but-2-en-1-one (2.7 g, 13.1 mmol) in toluene (28 ml) was treated with p-toluenesulfonic acid monohydrate (70 mg, 0.37 mmol), refluxed during 18 h and poured into water. The water phase was extracted three times with diethyl ether and the combined org. phases were washed with a saturated aqueous solution of sodium bicarbonate, dried (MgSO$_4$) and concentrated. FC (400 g SiO$_2$, hexane/diethylether 90:0.5) of the crude product (3.2 g, 64:36 mixture of (E)-1-(2-isobutylcyclohex-1-enyl)but-2-en-1-one (B)/(E)-1-(2-isobutylcyclohex-2-enyl)but-2-en-1-one (A)) gave a first fraction (0.31 g, 11%, 10:90 B/A), a second fraction (0.52 g, 19%, 71:29 B/A), and a third fraction (0.39 g, 14%, 91:9 B/A).

Data of the Third Fraction:

Boiling point: 75° C. (0.07 mbar).

IR: ν$_{max}$ 2951, 2928, 2867, 2838, 1650, 1628, 1440, 1366, 1289, 1249, 1170, 1139, 1115, 1061, 1017, 972, 934, 818, 766 cm$^{-1}$.

Odour description: geranium-like (fruity, rosy, green, metallic, herbaceous, woody).

EXAMPLE 4

Fragrance Composition

| Compound/Ingredient | part by weight 1/700 |
| --- | --- |
| Dimethyl Benzyl Carbinyl Acetate | 55 |
| Nopyl Acetate | 55 |
| Verdyl Acetate | 15 |
| Acetyl Isoeugenol | 5 |
| Hexyl Cinnamic Aldehyde | 95 |
| 10-Undecen-1-al | 5 |
| Allyl Caproate | 2 |
| Citronellol | 30 |
| Dihydro Myrcenol | 50 |
| Diphenyloxide | 4 |
| Dipropylene Glycol (DPG) | 28 |
| Ebanol ® (3-methyl-5-(2,2,3-trimethyl-3-cyclopenten-1-yl)-4-penten-2-ol) | 5 |
| Evernyl | 2 |
| 3Z-Hexen-1-ol | 1 |
| Iso E Super (1-(1,2,3,4,5,6,7,8-octahydro-2,3,8,8-tetramethyl-2-naphthalenyl)-ethanone) | 80 |
| Labienoxime 1% IPM*-TEC** at 10% in DPG | 8 |
| Lilial | 45 |
| Linalool | 45 |
| 4-(4-methoxypbenyl)-butan-2-one at 10% in DPG | 8 |
| Myraldene (CAS 37677-14-8) | 3 |
| Peche pure (5-heptyldihydro-2(3H)-furanone) | 5 |
| Serenolide ™ | 50 |
| Tetrahydro Linalol (3,7-dimethyl-octan-3-ol) | 55 |
| Undecavertol (4-methyl-3-decen-5-ol) | 4 |
| (E)-1-(2-isobutylcyclohex-1/2-enyl)but-2-en-1-one (from Example 2) | 45 |

*IPM = isopropylmyristate
**TEC = triethylcitrate 45 parts of a mixture of (E)-1-(2-isobutylcyclohex-1/2-enyl)but-2-en-1-one makes the above composition more fruity juicy, pushing the peachy character, providing to the floralcy a touch of originality/eccentricity.

EXAMPLE 5

Fragrance Composition

| Compound/Ingredient | parts by weight 1/900 |
| --- | --- |
| 4-tert-Butylcyclohexyl Acetate | 55 |
| Amyl Cinnamic Aldehyde | 140 |
| Allyl Amyl Glycolate (allyl 2-(2-methylbutoxy)acetate) | 8 |
| Methyl Anthranilate | 5 |
| Belambre [1] at 50% in IPM | 9 |
| Ethylene Brassylate | 150 |
| Alpha Damascone | 3 |
| Dihydro Myrcenol | 50 |
| Dipropylene Glycol (DPG) | 47 |
| Evernyl | 2 |
| Galaxolide at 50% in IPM | 150 |
| Galbanone [2] 10 (CAS 56973-85-4) | 8 |
| Geranium Essential oil | 2 |
| Isocyclocitral (CAS 1335-66-6) | 3 |
| Lilial | 150 |
| 2-Methyl-4-propyl-oxathiane at 50% in TEC | 2 |
| Rosemary Essential oil | 10 |
| Serenolide ™ [3] | 60 |
| Tetrahydro Linalol (3,7-dimethyl-octan-3-ol) | 30 |
| Veloutone (2,2,5-trimethyl-5-pentyl-cyclopentanone) | 8 |
| (E)-1-(2-isobutylcyclohex-1/2-enyl)but-2-en-1-one (from Example 2) | 8 |

[1] (1R,2S,2'S,4R)-1,7,7-Trimethyl-2'-(1-methylethyl)spiro[bicyclo[2.2.1]heptane-2,4'-[1,3]dioxane]; origin: Givaudan SA
[2] 1-(5,5-dimethylcyclohex-1-enyl)pent-4-en-1-one; origin: Givaudan SA
[3] 2-(1-(3,3-dimethylcyclohexyl)ethoxy)-2-methylpropyl cyclopropanecarboxylate; origin: Givaudan SA 8 parts of (E)-1-(2-isobutylcyclohex-1/2-enyl)but-2-en-1-one brings volume and diffusion to the composition, enhancing the floral geranium side and make it more lively.

The invention claimed is:

1. A compound of formula (I)

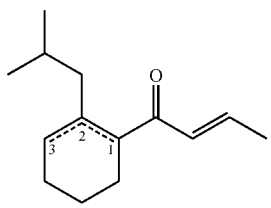
(I)

wherein
the bond between C-1 and C-2 is a single bond and the dotted line together with the bond between C-2 and C-3 represents a double bond; or
the bond between C-2 and C-3 is a single bond and the dotted line together with the bond between C-1 and C-2 represents a double bond.

2. A fragrance composition comprising a compound of formula (I) as defined in claim 1.

3. A method of improving, enhancing or modifying a fragrance composition or fragrance application comprising the step of incorporating a compound of formula (I) as defined in claim 1 in a base material.

* * * * *